(12) United States Patent
Morrison

(10) Patent No.: US 6,930,774 B1
(45) Date of Patent: Aug. 16, 2005

(54) METHOD AND APPARATUS FOR PRODUCING UNIQUE RADIATION SPECTRA

(76) Inventor: David A. Morrison, 11 Cortland Dr., Hudson, MA (US) 01749

( * ) Notice: Subject to any disclaimer, the term of this patent is extended or adjusted under 35 U.S.C. 154(b) by 80 days.

(21) Appl. No.: 10/427,533

(22) Filed: May 1, 2003

Related U.S. Application Data

(60) Provisional application No. 60/376,439, filed on May 1, 2002.

(51) Int. Cl.[7] .............................. G01J 3/10; G01J 3/18
(52) U.S. Cl. .......................................... 356/310; 362/2
(58) Field of Search ................................ 356/310, 326, 356/328, 330, 331, 332, 333, 334; 362/2

(56) References Cited

U.S. PATENT DOCUMENTS

| | | | | |
|---|---|---|---|---|
| 3,586,442 A | * | 6/1971 | Tripp | 356/331 |
| 3,907,430 A | * | 9/1975 | Mann | 356/332 |
| 4,247,202 A | * | 1/1981 | Failes | 356/310 |
| 4,290,699 A | * | 9/1981 | Idelson | 356/420 |
| 4,740,082 A | * | 4/1988 | Young | 356/451 |
| 4,929,078 A | * | 5/1990 | Harmon | 356/320 |
| 5,090,807 A | * | 2/1992 | Tai | 356/310 |
| 6,046,808 A | | 4/2000 | Fateley | |
| 6,128,078 A | | 10/2000 | Fateley | |
| 6,392,748 B1 | | 5/2002 | Fateley | |
| 6,665,068 B1 | * | 12/2003 | Schoeppe et al. | 356/310 |
| 2002/0176149 A1 | | 11/2002 | Davis et al. | |

OTHER PUBLICATIONS

Deverse, R.A. et al., Application of Digital Micro-Mirror Arrays in Spectrometry and Imaging, published at www.threelc.com/PITT2002_files/slide0044.htm.

* cited by examiner

*Primary Examiner*—F. L. Evans
(74) *Attorney, Agent, or Firm*—James A. Sheridan; Dahl & Osterloth, LLP

(57) ABSTRACT

Apparatus and methods are disclosed for providing a desired spectral intensity profile from a broadband light source. The apparatus comprises separation means for separating light provided by the broadband light source into radiation having a continuum of wavelengths; a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass from the first side to the second side, wherein the portion of the radiation conforms to the desired blocking contour; and recombination means for recombining the portion of the radiation conforming to the desired blocking contour into the desired spectral intensity profile.

26 Claims, 8 Drawing Sheets

METHOD AND APPARATUS FOR PRODUCING UNIQUE RADIATION SPECTRA

REFERENCE TO PENDING PRIOR PATENT APPLICATION

This patent application claims benefit of pending prior U.S. Provisional Patent Application Ser. No. 60/376,439, filed May 1, 2002 by David A. Morrison for METHOD AND APPARATUS FOR PRODUCING UNIQUE RADIATION SPECTRA, which patent application is hereby incorporated herein by reference.

FIELD OF THE INVENTION

This invention is related to optical light source apparatus and methods in general, and more particularly to apparatus and methods for providing unique radiation spectra.

BACKGROUND OF THE INVENTION

It has become apparent, particularly in the field of biological sciences, that there exists a need for radiation sources that can be customized so as to produce a spectrum possessing a set of desired characteristics. This need ranges from illuminating a sample for microscopic evaluation to producing a desired spectrum for the purpose of designed stimulation of cellular activity.

Although there are methods to produce bands of spectra using interference filters, or some variation of spectra separation as used in spectroscopes, these methods exhibit the common deficiency of only permitting contiguous bands of energy to reach the sample. Additionally, these methods are designed to produce discrete bands with sharp frequency cut-offs and eliminate all radiation outside of these bands. Some research or analytical applications require many of these expensive and fragile filters to conduct routine laboratory evaluations.

SUMMARY OF THE INVENTION

The fundamental concept of the invention is to use a broadband source of energy, separate it into a continuum of wavelengths, eliminate all or a portion of the radiation at any wavelength, and then recombine the remaining energy to be delivered to the sample or target, thereby creating a new spectrum possessing desired and advantageous characteristics.

An object of the invention is to provide apparatus for producing desired radiation spectra.

Another object of the present invention is to provide apparatus for producing desired radiation spectra, which are scalable to high powers.

And another object of the present invention is to provide apparatus for producing the desired radiation spectra in which the apparatus comprises relatively low-cost components.

A further object of the invention is to provide apparatus for producing desired radiation spectra used in conjunction with scientific devices for biological analysis.

A still further object is to provide apparatus for producing desired radiation spectra used in conjunction with devices for the entertainment industry.

Yet another object is to provide a method for producing desired radiation spectra.

Still another object is to provide a method for producing the desired radiation spectra in which low-cost components are used.

With the above and other objects in view, as will hereinafter appear, there is provided an apparatus for providing a desired spectral intensity profile from a broadband light source, the apparatus comprising: separation means for separating light provided by the broadband light source into radiation having a continuum of wavelengths; a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour; and recombination means for recombining the portion of the radiation conforming to the desired blocking contour into the desired spectral intensity profile.

In accordance with a further feature of the invention there is provided a system for analysis of a specimen using a desired spectral intensity profile from a broadband source, the system comprising: apparatus for providing a desired spectral intensity profile from a broadband light source, the apparatus comprising: separation means for separating light provided by the broadband light source into radiation having a continuum of wavelengths; a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour; and recombination means for recombining the portion of the radiation conforming to the desired blocking contour into the desired spectral intensity profile; and an optical illumination pathway having an input end and an output end, the input end configured to receive the radiation having the desired spectral intensity profile from the recombination means, and the output end being configured to provide the radiation having the desired spectral intensity profile to a microscope.

In accordance with a further feature of the invention there is provided a method for producing a desired spectral intensity profile from a broadband light source, the method comprising: separating light provided by the broadband light source into radiation having a continuum of wavelengths; blocking a portion of the radiation separated into the continuum of wavelengths so as to allow a remaining portion of the radiation to pass through a blocking element, wherein the remaining portion conforms to a desired blocking contour provided by the blocking element; and recombining the remaining portion of the radiation conforming to the desired blocking contour so as to create a desired spectral intensity profile.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

Figure 1:
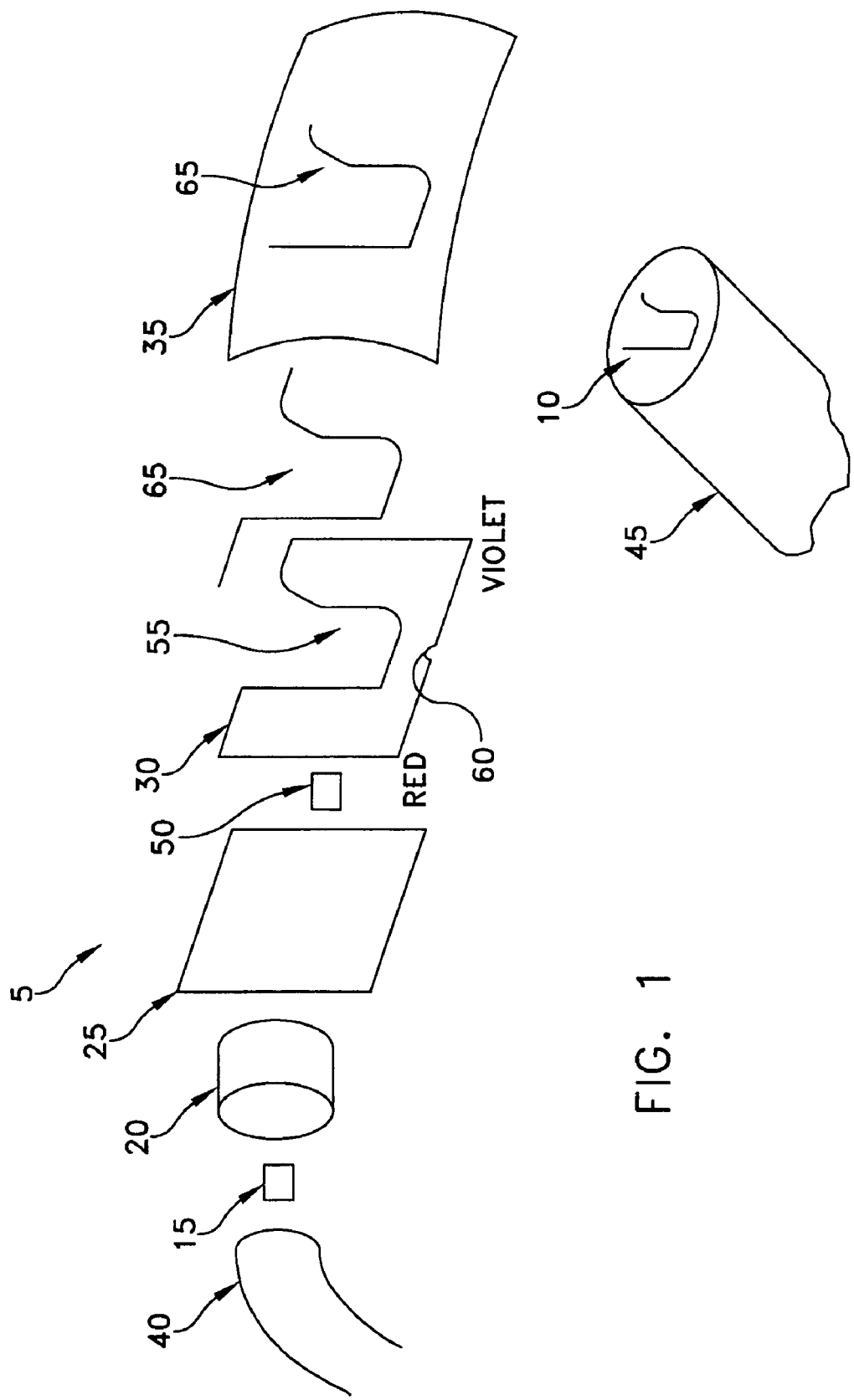
FIG. 1 is a schematic view of one form of a spectral profiling device, illustrative of a preferred embodiment of the invention.

Referring to FIG. 1, and in a preferred embodiment of the present invention, there is shown a spectral profiling device 5 for producing various desired spectra 10 from broadband light 15. Spectral profiling device 5 includes a lens assembly 20, a transmissive holographic grating 25, a blocking element 30, a toroidal mirror 35 arranged in series with respect to one another. Spectral profiling device 5 is configured to receive broadband light from an input fiber optic bundle 40 and to provide a desired spectral intensity profile 10 to an output fiber optic bundle 45. In turn, output fiber optic bundle 45 is used to produce illumination for a given device. This given device may include, for example, a sample stage of a microscope (not shown).

In an alternative preferred embodiment of the present invention, a ruled reflective grating or a ruled transmissive grating is used in spectral profiling device 5 in place of transmissive holographic grating 25.

The energy exiting fiber optic bundle 40 is collimated by lens assembly 20 and then projected onto transmissive holographic grating 25. The energy transmitted by transmissive holographic grating 25 is then diffracted to produce a rectangularly shaped continuum of color 50 such as from red to violet, which illuminates blocking element 30.

Still referring to FIG. 1, and in a preferred embodiment of the present invention, blocking element 30 comprises an opaque material and is configured to provide a desired contour 55. Preferably, blocking element 30 comprises a thin metal sheet which is cut by a precision laser cutting system. A precisely placed reference detent 60 in blocking element 30 provides the correct correlation of and blocking element 30 and rectangular shaped continuum of color 50 with respect to one another. Reference detent 60 is configured to correspond with a holder (not shown). Blocking element 30 and its holder (not shown) are designed with adequate width and height to prevent any sidebands, secondary orders from the diffraction grating, or stray light to enter the optical path.

The energy allowed to pass blocking element 30 has a given spectral intensity profile 65. Spectral intensity profile 65 then strikes toroidal mirror 35. Toroidal mirror 35 acts to bring spectral intensity profile 65 to the correct scale so as to produce desired spectral intensity profile 10. Toroidal mirror 35 also acts to reposition desired spectral intensity profile 10 into an input end of output fiber optic bundle 45. Desired spectral intensity profile 10 is delivered through output fiber optic bundle 45 to a microscope (not shown).

In a preferred embodiment of the present invention, input fiber optic bundle 40, lens assembly 20, transmissive holographic grating 25, toroidal mirror 35, and output fiber optic bundle 45 are all aligned and permanently mounted with respect to one another so as to form a robust design of spectral profiling device 5.

Referring still to FIG. 1, and in a preferred embodiment of the present invention, spectral profiling device 5 may comprise commercially available components. Fiber optic bundle 45 may be selected from components sold by Dolan-Jenner Inc. of Haverhill, Mass. Fiber optic bundle 40 is typically used to produce illumination for the sample stage of a microscope, such as those sold by Carl Zeiss of Thornwood, N.Y. Lens transmissive holographic grating 25 may also be selected from commercially available components supplied by Holographix LLC, of Hudson, Mass. Desired contour 55 of blocking element 30 may be cut by a precision laser cutting system sold by Alase Technologies of Pepperell, Mass. Toroidal mirror 35 may also be selected from commercially available components, such as those sold by ARW Optical of Wilmington, N.C. Output fiber optic bundle 45 may be selected from commercially available components, such as those sold by Edmund Scientific of Barrington, N.J. With these commercially available components, and other components fabricated at low cost, spectral profiling device 5 provides a relatively low-cost system to create desired spectral intensity profile 10.

For biological cellular analysis, broadband source 15 is provided by a flexible fiber optic illuminator optically coupled onto an optical microscope. The output of the fiber optic illuminator is removed from the microscope and collimated by lens assembly 20 and then dispersed by transmissive holographic grating 25 into a pseudo-rectangular shape as required for the blocking element as previously described.

The energy that is passed by the blocking element is reformed by a toroidal mirror, and projected onto the input end of a fiber bundle as originally used to carry the light to the microscope. The output end of the fiber bundle is constructed to the same physical requirements as the original bundle, and therefore simply inserted as a replacement source, but now with an infinitely modifiable spectrum.

Figure 2:
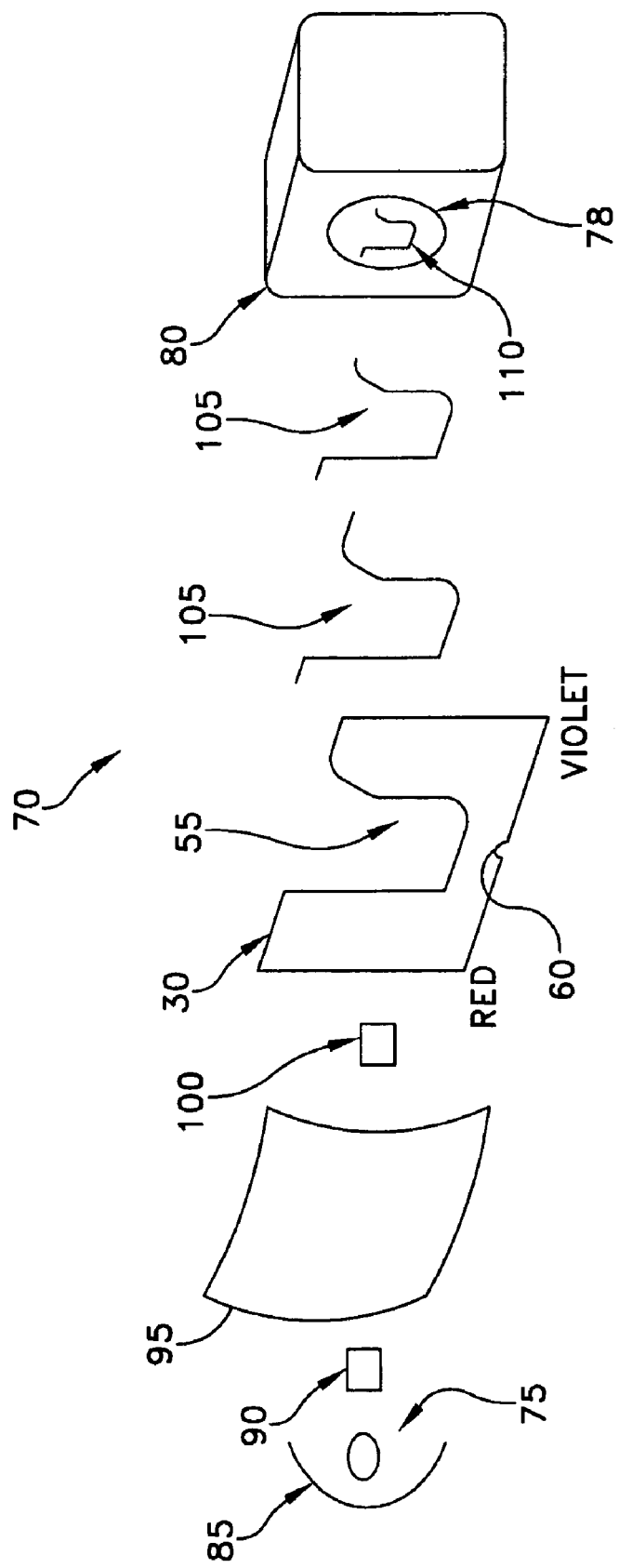
FIG. 2 is a schematic view of another form of a spectral profiling device receiving direct radiation from a broadband light source and providing direct coupling to an optical illumination pathway.

Referring now to FIG. 2, and in a preferred embodiment of the present invention, there is shown a direct radiation and direct coupling spectral profiling device 70 for producing various desired spectra from a direct radiation source 75, which in turn is directly coupled with a beam homogenizer 78 at an input port of an optical illumination pathway 80 of a microscope (not shown). Broadband white-light source 75 is positioned in a parabolic reflector 85 so as to project a reasonably collimated beam of energy 90. Projected collimated beam 90 passes through a toroidal transmissive holographic grating 95 so as to produce a diffracted rectangularly shaped continuum of color 100, which is preferably from red to violet. Blocking element 30 is positioned between toroidal transmissive holographic grating 95 and optical illumination pathway 80 so as to intercept a portion of continuum of color 100.

Still referring to FIG. 2, and in a preferred embodiment of the present invention, blocking element 30 comprises an opaque material and is configured to provide a desired contour 55. Preferably, blocking element 30 comprises a thin metal sheet which is cut to comprise desired contour 55 by a precision laser cutting system. A precisely placed reference detent 60 in blocking element 30 provides the correct correlation of blocking element 30 and continuum 100 with respect to one another when blocking element 30 is mounted in its holder (not shown). Blocking element 30 and its holder (not shown) are designed to provide adequate width and height so as to prevent any sidebands and/or secondary orders from the diffraction grating, or any stray light from entering the optical path.

The energy that is allowed to pass blocking element 30 has a given spectral intensity profile 105. The optical power of the toroidal diffraction grating 95 progressively reduces given spectral intensity profile 105 until the scale is reduced to a desired spectral intensity profile 110 so as to enter beam homogenizer 78 at the input port of the microscope's illumination optical pathway 80.

Referring still to FIG. 2, and in a preferred embodiment of the present invention, direct radiation and direct coupling spectral profiling device 70 may comprise commercially available components. Broadband white-light source 75 and parabolic reflector 85 may be selected from those sold by Oriel Corporation of Stratford, Conn. Toroidal transmissive holographic grating 95 may also be selected from those manufactured by JobinYvon of Edison, N.J. With these commercially available components, other fabricated components at low cost, direct radiation and direct coupling spectral profiling device 70 is a relatively low-cost system to create desired spectral intensity profile 110.

Figure 3:
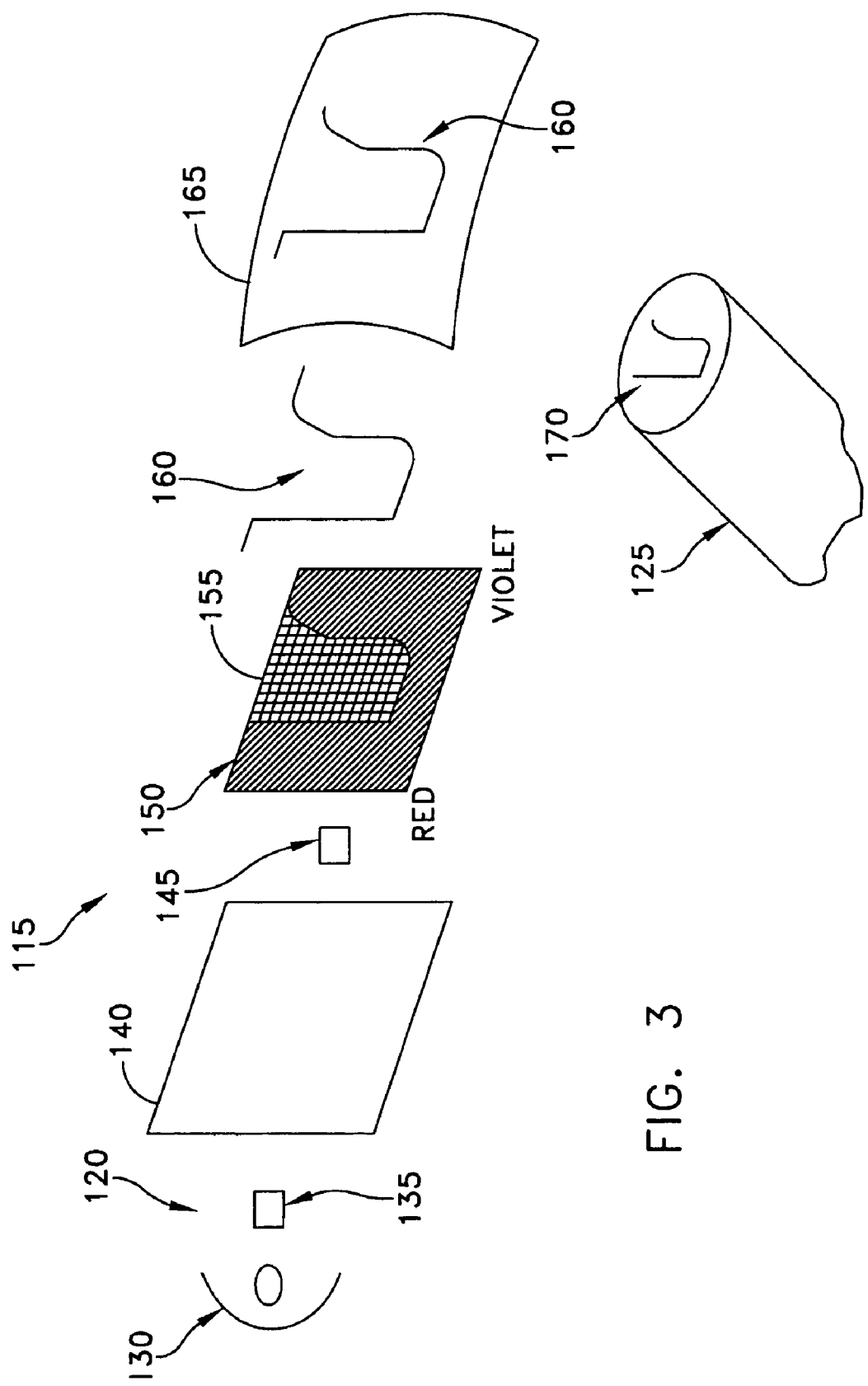
FIG. 3 is a schematic view of a spectral profiling device comprising a 2D transmissive light-valve array.

Referring now to FIG. 3, and in a preferred embodiment of the present invention, there is shown a direct radiation and fiber optic coupling spectral profiling device 115 for producing from a direct radiation source 120 various desired spectra, which are coupled through a fiber optic coupling 125 to a microscope. Broadband white-light source 120 is positioned in a parabolic reflector 130 so as to project a reasonably collimated beam of energy 135. Projected collimated beam 135 then passes through a transmissive holographic grating 140 so as to produce a diffracted, rectangularly shaped continuum of color 145, which preferably ranges from red to violet. The continuum 145 is then intercepted by a blocking element 150. Blocking element 150 comprises a 2-D transmissive light-valve array 155. 2-D transmissive light-valve array 155 comprises hundreds of addressable cells positioned in an orthogonal arrangement. By computer control, or through the operation of an array controller, pre-selected combinations of the addressable cells are selectively transmissive. This pre-selected combination of cells then creates a spectral intensity profile 160, which passes therethrough to toroidal mirror 165. Toroidal mirror 165 acts to bring spectral intensity profile 160 to the correct scale and to illuminate the input end of the fiber optic bundle 125. A desired spectral intensity profile 170 is provided through fiber optic bundle 125 to a microscope (not shown).

Referring still to FIG. 3, and in a preferred embodiment of the present invention, direct radiation and fiber optic coupling spectral profiling device 115 may comprise commercially available components. Broadband white-light source 120 and parabolic reflector 130 may be selected from those sold by Oriel Corporation of Stratford, Conn. Transmissive holographic grating 140 may also be selected from those manufactured by Holographix LLC, of Hudson, Mass. Blocking element 150, which comprises 2-D transmissive light-valve array 155 may be obtained from CRI Incorporated of Woburn, Mass. Toroidal mirror 165 may be selected from those sold by ARW Optical Company of Wilmington, N.C. Fiber optic bundle 125 may be selected from those manufactured by Edmund Scientific of Barrington, N.J. With these commercially available components and other low-cost fabricated components, direct radiation and fiber optic coupling spectral profiling device 115 is a relatively low-cost system for creating desired spectral intensity profile 170.

Figure 4:
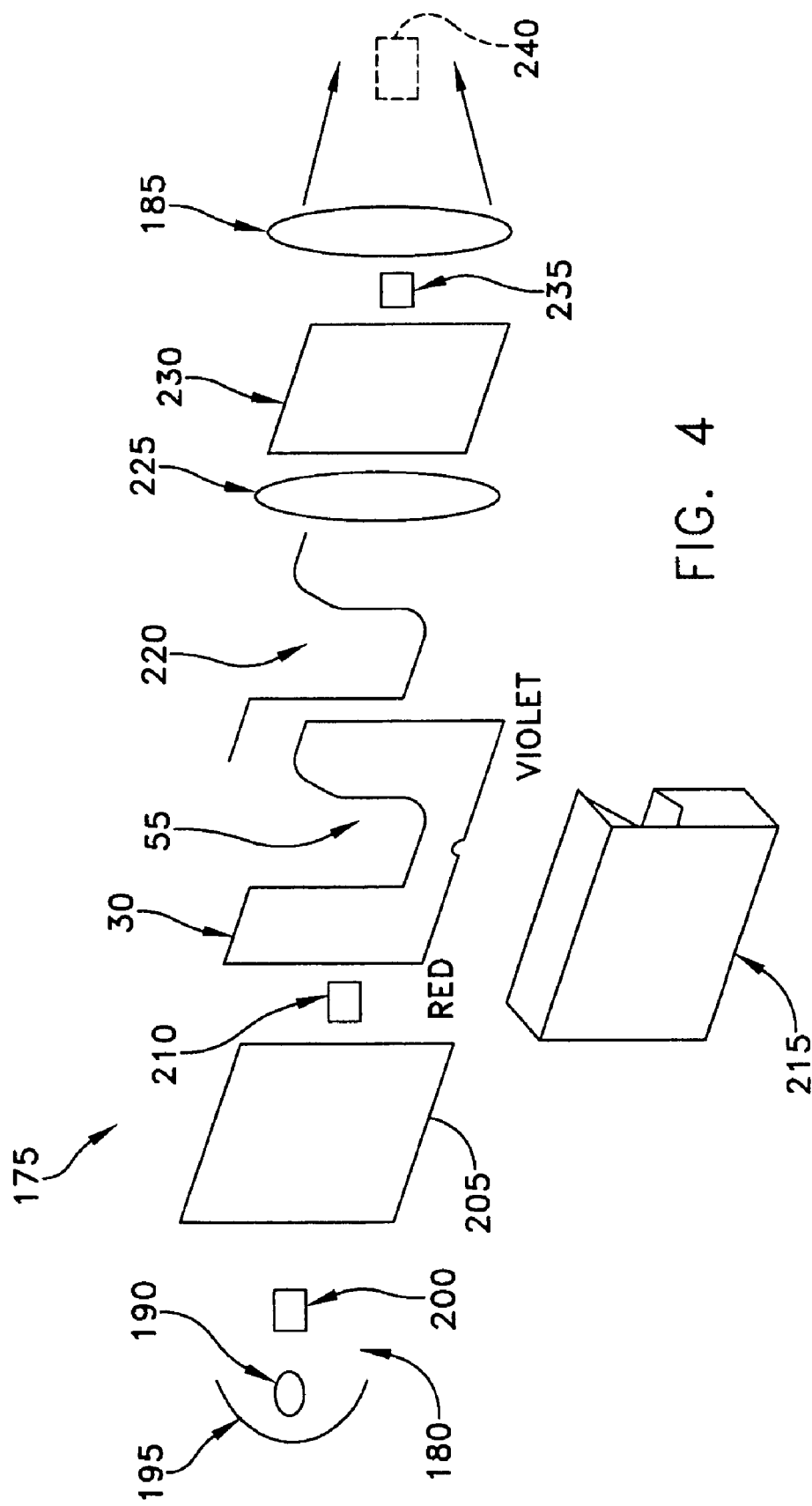
FIG. 4 is a schematic view of a spectral profiling device for stage and studio lighting.

Referring now to FIG. 4, and in a preferred embodiment of the present invention, there is shown a stage and studio lighting spectral profiling device 175 for producing from a direct radiation source 180 various desired spectra, which in turn are coupled to a studio lighting lens 185. A high-power broadband white-light source 190 is positioned in a parabolic cold mirrored reflector 195 so as to project a reasonably collimated beam of energy 200. Projected collimated beam of energy 200 then passes through transmissive holographic grating 205 so as to produce a diffracted, rectangularly shaped continuum of color 210, which preferably ranges from red to violet.

Blocking element 30 is configured to intercept continuum 210. Blocking element 30 comprises an opaque material and is configured to provide a desired contour 55. Preferably, blocking element 30 comprises a thin sheet of metal which is cut by a precision laser cutting system to create desired contour 55. Blocking element 30 further comprises a high reflectivity coating and is mounted at an angle with respect to the path of projected collimated beam 200 so as to reflect unwanted spectral energy into a light trap 215. Light trap 215 provides an area where the unwanted energy can be diffused and dissipated. A precisely placed detent 60 provides the correct correlation of blocking element 30 and continuum 210 with respect to one another when blocking element 30 is mounted in its holder (not shown).

Energy that is allowed to pass by blocking element 30 has a desired spectral intensity profile 220. Lens 225 directs the light of desired spectral intensity profile 220 through a light shaping diffuser 230 so as to produce slightly diffused spectra 235. Light shaping diffuser 230 is a highly transmissive element which is configured to project slightly diffused spectra 235 project to lens 185. Preferably, lens 185 is a long focal length lens typically used in studio lighting designs so as to project the integrated color of spectra 235 to a stage area of interest 240.

Referring still to FIG. 4 and in a preferred embodiment of the present invention stage and studio lighting spectral profiling device 175 may comprise commercially available components. High-power broadband white-light source 190 may be selected from those sold by Luxtel of Danvers, Mass. Parabolic cold mirrored reflector 195 may be selected from those sold by Opti-Forms Inc. of Temecula, Calif. Transmissive holographic grating 205 may be selected from those sold by Holographix LLC of Hudson, Mass. Blocking element 30 is preferably cut to desired contour 55 by a precision laser cutting system sold by Alase Technologies of Pepperell, Mass. Lens 185 and lens 225 may be selected from components sold by Edmund Scientific of Barrington, N.J. Light shaping diffuser 230 can be obtained from Physical Optics Corporation of Torrance, Calif. With these commercially available components, and other components fabricated at low cost, stage and studio lighting spectral profiling device 175 is a relatively low-cost system for creating slightly diffused spectra 235.

Figure 5:
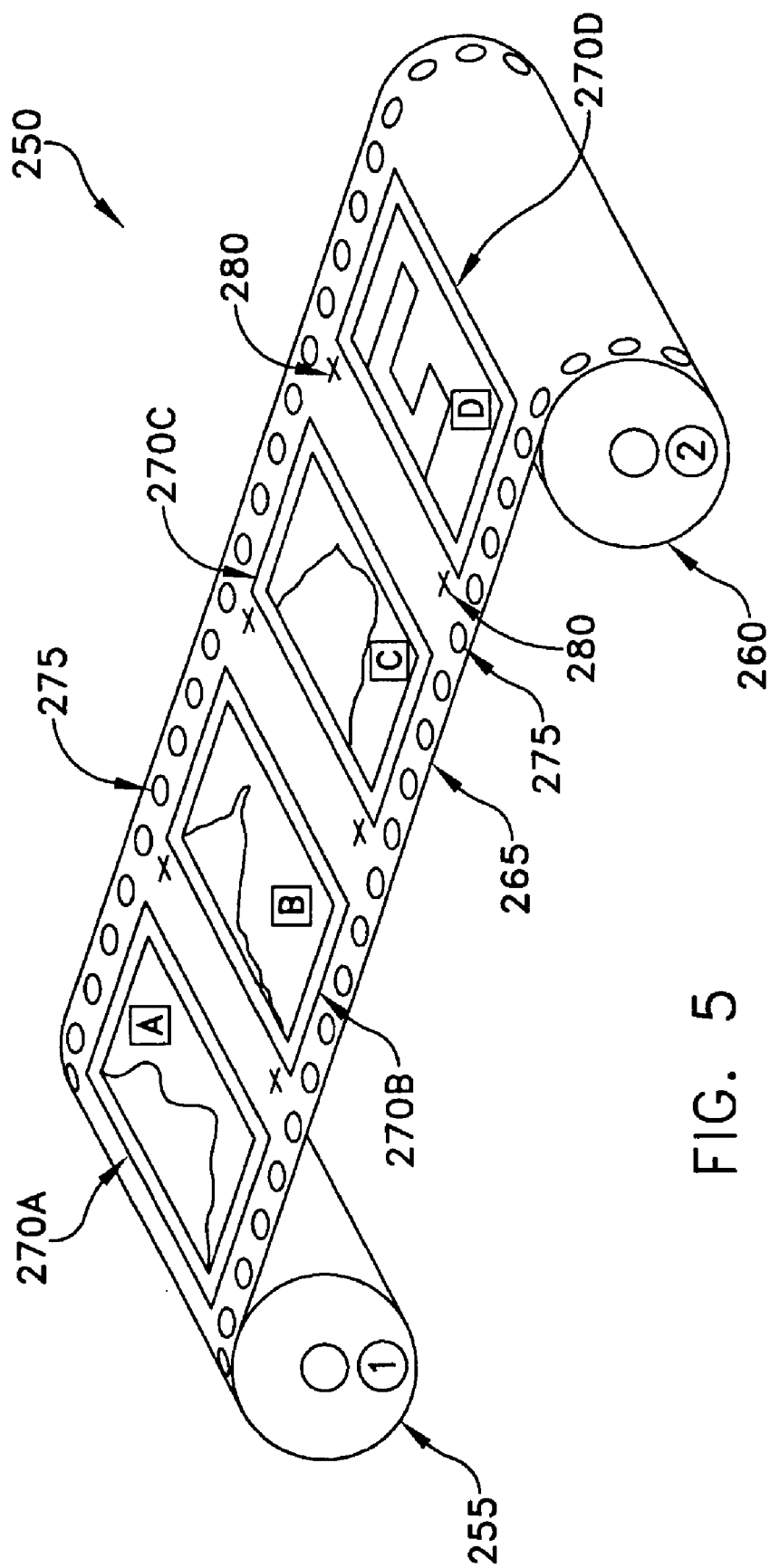
FIG. 5 is a schematic view of a selectively positionable web having a plurality of selectable blocking elements thereon.

Looking now at FIG. 5, and in a preferred embodiment of the present invention, there is shown a carrier device 250 having a supply roll 255 and a take-up roll 260 with a web of material 265 being supported therebetween for selectively providing storage and access to a plurality of blocking elements 270A–270D. Preferably, carrier device 250 is used in conjunction with a protective enclosure and configured with one of the spectral profiling devices described herein, such as a spectral profiling. Preferably, material 265 comprises continuous web of opaquely coated polyester with a perforated edge 275 so as to provide transport and positioning when placed into the enclosure. A set of fiducial marks 280 placed in or on web 265, are created at the same time as the contour on blocking elements 270A–270D so as to provide accurate positioning. The transport and positioning can be manual or automatically selected. Blocking elements 270A–270D are created by selectively removing the opaque material by processing, etching, or ablating to obtain the desired contours.

Figure 6:
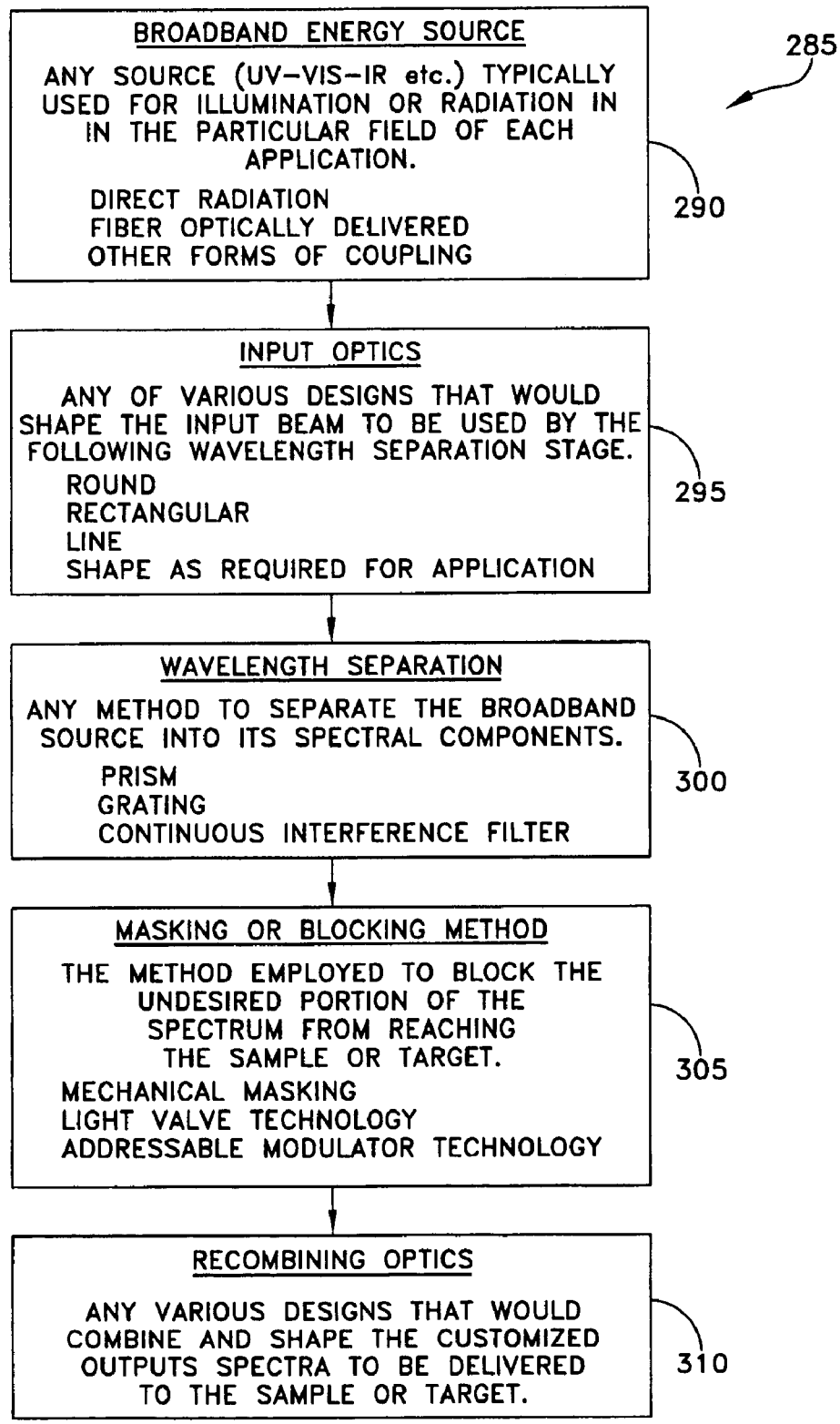
FIG. 6 is a diagrammatic illustration of a flow chart illustrating combinations of components used in preferred embodiments of the present invention.

Referring to FIG. 6, there is shown a block diagram 285 identifies a series of steps for producing desired radiation spectra using preferred embodiments of the present invention. Block 290 identifies a preferred group of broadband energy sources. Block 295 identifies a preferred group of input optics. Block 300 identifies a group of preferred wavelength separation devices. Block 305 identifies a group of preferred blocking methods. Block 310 identifies recombining optics used in a final step.

In another embodiment of the present invention (not shown), for laboratory microscope illumination, a quartz tungsten halogen lamp is used as a broadband visible 'white light' source. The output beam of the lamp is passed through a lens to produce a reasonably collimated source of radiation. The collimated beam is then passed through an equilateral prism to produce a separation of the 'white light' into a continuum of color, representing the spectral content of the white light source. A second lens is used, either before or after the prism so as to shape the color spectrum into a rectangle of uniform intensity and spectrally separated energy. Preferably, the rectangle of energy comprises a wavelength axis having a greater length than the intensity axis so as to provide adequate wavelength discrimination by the blocking element used further along in the optical path. This projected rectangle of energy is then intercepted by a blocking element. The blocking element, in its simplest form, is a rectangle of thin metal, dimensionally similar to the rectangle of projected energy. The blocking element is configurable for accurate, repeatable placement. The blocking element is specifically contoured, such as required for fluorescence microscopy, to eliminate predetermined amounts of spectral intensity across the entire desired wavelength band. The contour also permits and acts to correct any intensity variations in the source. The spectral intensity allowed to pass the blocking element passes through one or more additional lenses so as to alter its cross-sectional shape prior to illumination of a microscope. Preferably, the lamp position, prism, lenses along the optical path, and the blocking element are mechanically positioned for a compact robust design.

A low-cost narrow band filter is assembled onto a blocking element having a known pass-band and is provided for validating the correct wavelength relationship of the blocking element and the spectrum produced by the prism. Using this arrangement, energy is only transmitted when the position of the blocking element is correctly aligned with the spectrum produced by the prism. This embodiment performs a function similar to individual interference filters at approximately 1/10 the cost. Also, due to the infinite number of contours possible, the ability to pass 100% of the incident energy at any wavelength, totally eliminate side-bands, and simultaneously provide discrete bands of separated energy from one source is possible. This embodiment is able to outperform interference filters in most design requirements. In addition, these advantages are even more valuable in the UV spectrum, where interference filters suffer from low throughput.

In another preferred embodiment of the present invention (not shown), a broadband source as described herein, is collimated, and then formed into a rectangle of 'white light', which is then used to uniformly radiate a 'linear variable filter' (continuous interference filter). This is a filter that provides a spectral continuum by continuously varying the internal design elements along one axis, thereby passing specific wavelengths along that axis, while blocking all other wavelengths.

The other axis is an axis of uniform transmittance. A blocking element as described herein is juxtapositioned in front of or behind the filter so as to provide the preferred spectral intensity modification. The transmitted energy is then optically collected and shaped into the required dimensions to become the input beam to a microscope. As above, the mechanics of construction are designed for stable and robust operation.

Figure 7:
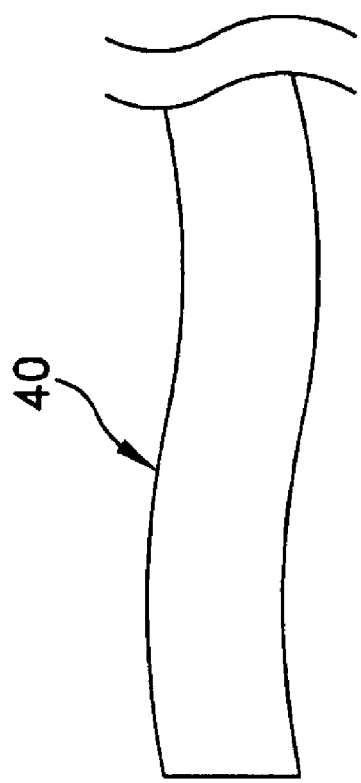
FIG. 7 is a schematic view of a single element LED light source.
Figure 7:
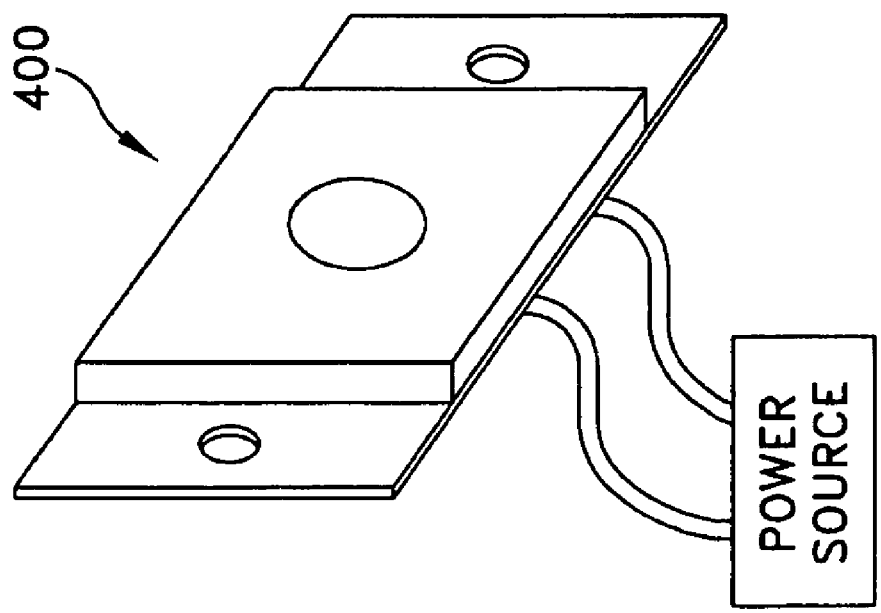

Referring now at FIG. 7, and in a preferred embodiment of the present invention, there is shown a broadband LED 400, used to illuminate the input ends of a multi-fiber optical assembly 40. Alternatively, a series of less broad LEDs are used to illuminate the input ends of a multi-fiber optical assembly. The fibers are optically mixed and formed into a bundle. The output of the bundle is then collimated and used to illuminate a prism or diffraction grating as described above. The energy is formed into a rectangle and projected onto a light valve array. As described herein above, the energy that is passed through the array is optically collected and directed to the sample or target.

Figure 8:
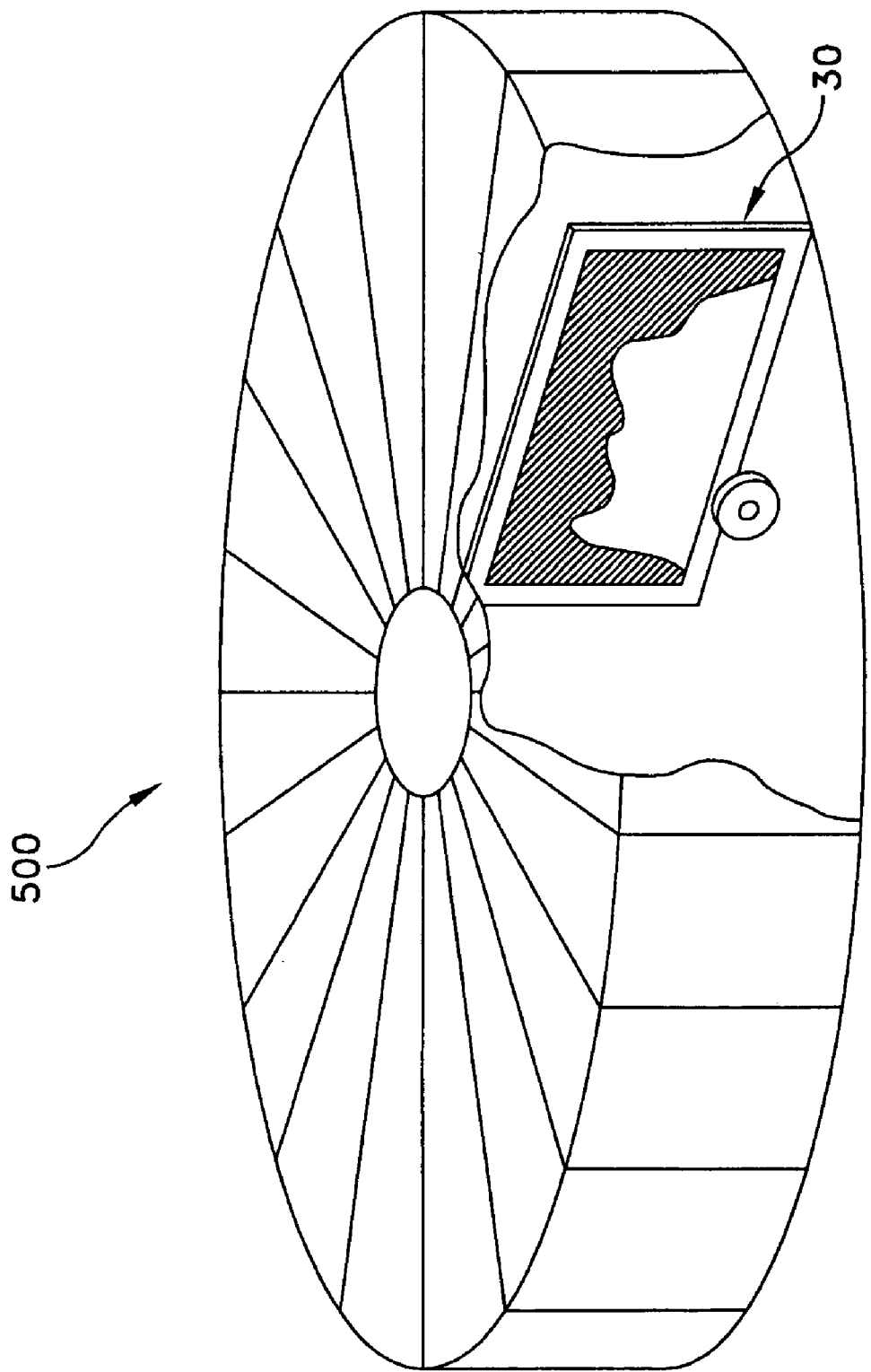
FIG. 8 is a schematic view of a blocking element supply carousel.

Referring now to FIG. 8, and in a preferred embodiment of the present invention, there are shown mechanical blocking elements 30 configured for selective use from a storage carousel 500 or an equivalent structure. In a preferred embodiment of the present invention, a computer or controller is used for remote selection and use of mechanical blocking elements 30.

Additionally, in a preferred embodiment of the present invention (not shown), mechanical blocking elements may be configured for selective use from a storage carousel or an equivalent structure. In a preferred embodiment of the present invention, a computer or controller is used for remote selection and use of the mechanical blocking elements.

In is further envisioned that other combinations of the above elements may be made practical for other applications throughout the UV-Visible-IR range. Additionally, portions of the spectrum may be optically magnified to produce more critical embodiments, or the lamps themselves may only output over a limited range of the spectrum. However, the fundamental concept of the invention of using a broadband source of energy, separating it into a continuum of wavelengths, eliminating, all of, or some lesser portion of, the radiation at any wavelength, and then recombining the remaining energy for delivery to the sample or target is consistent with each of the preferred embodiments of the present invention.

What is claimed is:

1. Apparatus for providing a desired spectral intensity profile to an optical device from a broadband light source, the apparatus comprising:
   separation means for separating light provided by the broadband light source into radiation having a continuum of wavelengths;
   a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour; and
   recombination means for recombining the portion of the radiation conforming to the desired blocking contour into the desired spectral intensity profile;
   wherein the recombination means comprise a lens and a light shaping diffuser, the light shaping diffuser is configured to cause the radiation to change from a first cross-sectional dimension to a second cross-sectional dimension, the first cross-sectional dimension of the radiation conforms to a first shape of the blocking element, and the second cross-sectional dimension of the radiation conforms to a second shape of the optical device configured to receive the desired spectral intensity profile.

2. Apparatus according to claim 1 wherein the separation means comprise a lens assembly and transmissive holographic grating disposed in a pathway of broadband light between the broadband light source and the blocking element.

3. Apparatus according to claim 1 wherein the separation means comprise a toroidal transmissive holographic grating disposed in a pathway of broadband light between the broadband light source and the blocking element.

4. Apparatus according to claim 1 wherein the separation means comprise a transmissive holographic grating disposed in a pathway of broadband light between the broadband light source and the blocking element.

5. Apparatus according to claim 1 wherein the blocking element comprises a plate having the desired blocking contour in a static configuration therethrough.

6. Apparatus according to claim 5 wherein the plate further comprises a reference detent therein for aligning the desired blocking contour of the plate with the continuum of wavelengths of the radiation from the separation means.

7. Apparatus according to claim 1 wherein the blocking element comprises a two-dimensional light valve.

8. Apparatus according to claim 1 wherein the blocking element comprises an addressable modulator.

9. Apparatus according to claim 1 wherein the blocking element is selectively chosen from a group consisting of a plurality of unique blocking elements, wherein the desired blocking contour of each of the plurality of unique blocking elements is different from one another.

10. Apparatus according to claim 9 further comprising a roll of material containing the plurality of unique blocking elements thereon and configured for selectively disposing a chosen one of the plurality of unique blocking elements into a pathway of broadband light between the broadband light source and the recombination means.

11. Apparatus according to claim 9 further comprising a carousel configured for storing the plurality of blocking elements therein, the carousel configured for selective placement of a chosen one of the plurality of unique blocking elements into a pathway of broadband light between the broadband light source and the recombination means.

12. Apparatus according to claim 9 wherein the plurality of blocking elements are configured for manual selection of a chosen one of the plurality of unique blocking elements and manual placement of the chosen one of the plurality of unique blocking elements into a pathway of broadband light between the broadband light source and the recombination means.

13. Apparatus according to claim 9 wherein the plurality of blocking elements are configured for selection and placement by a computer of a chosen one of the plurality of unique blocking elements into a pathway of broadband light between the broadband light source and the recombination means.

14. A system for analysis of a specimen using a desired spectral intensity profile from a broadband source, the system comprising:
   apparatus for providing a desired spectral intensity profile from a broadband light source, the apparatus comprising:
      separation means for separating light provided by the broadband light source into radiation having a continuum of wavelengths;
      a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour; and
      recombination means for recombining the portion of the radiation conforming to the desired blocking contour into the desired spectral intensity profile; and
   an optical illumination pathway having an input end and an output end, the input end configured to receive the radiation having the desired spectral intensity profile from the recombination means, and the output end being configured to provide the radiation having the desired spectral intensity profile to a microscope.

15. A system according to claim 14 wherein the broadband light source comprises radiation from a high-power broadband light source.

16. A system according to claim 15 further comprising a parabolic reflector configured to direct the radiation from the high-power broadband light source in a light path toward the blocking element.

17. A system according to claim 14 wherein the broadband light source comprises a fiber optic illuminator and an input fiber optic line in optical connection to the separation means.

18. A system according to claim 14 wherein the broadband light source comprises at least one LED.

19. A system according to claim 14 wherein the optical illumination pathway comprises an output fiber optic line configured to receive the radiation having the desired spectral intensity profile from the recombination means and provide the radiation having the desired spectral intensity profile to the microscope.

20. A system according to claim 14 wherein the optical illumination pathway comprises an input window in the microscope.

21. A system for providing a desired spectral intensity profile to a studio lighting lens, the system comprising:
apparatus for providing a desired spectral intensity profile from a broadband light source, the apparatus comprising:
separation means for separating light provided by the broadband light source into radiation having a continuum of wavelengths;
a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour; and
recombination means for recombining the portion of the radiation conforming to the desired blocking contour into the desired spectral intensity profile;
a light trap configured to receive reflected light form the blocking element; and
wherein the recombination means comprise a light shaping diffuser.

22. A system according to claim 21 wherein the blocking element is positioned at an angle relative to a pathway of broadband light received from the separation means so as to direct light reflected from the blocking element at an angle toward the light trap.

23. A system according to claim 21 wherein the recombination means comprise a lens and the light shaping diffuser.

24. Apparatus for providing a desired spectral intensity profile to an optical device from a broadband light source, the apparatus comprising:
separation means for separating light provided by the broadband light source into radiation having a continuum of wavelengths;
a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour;
recombination means for recombining the portion of the radiation conforming to the desired blocking contour into the desired spectral intensity profile;
wherein the blocking element is selectively chosen from a group consisting of a plurality of unique blocking elements, wherein the desired blocking contour of each of the plurality of unique blocking elements is different from one another; and
a roll of material containing the plurality of unique blocking elements thereon and configured for selectively disposing a chosen one of the plurality of unique blocking elements into a pathway of broadband light between the broadband light source and the recombination means.

25. Apparatus for providing a desired spectral intensity profile to an optical device from a broadband light source, the apparatus comprising:
separation means for separating light provided by the broadband light source into radiation having a continuum of wavelengths;
a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour;
recombination means for recombining the portion of the radiation conforming to the desired blocking contour into the desired spectral intensity profile;
wherein the blocking element is selectively chosen from a group consisting of a plurality of unique blocking elements, wherein the desired blocking contour of each of the plurality of unique blocking elements is different from one another; and
a carousel configured for storing the plurality of blocking elements therein, the carousel configured for selective placement of a chosen one of the plurality of unique blocking elements into a pathway of broadband light between the broadband light source and the recombination means.

26. A system for analysis of a specimen using a desired spectral intensity profile from a broadband source, the system comprising:
apparatus for providing a desired spectral intensity profile from a broadband light source, the apparatus comprising:
separation means for separating light provided by the broadband light source into radiation having a continuum of wavelengths;
a blocking element having a first side and a second side, the first side having a two-dimensional surface with a desired blocking contour configured thereon, the blocking element positioned relative to the separation means so as to receive the radiation separated into the continuum of wavelengths onto the first side thereof and allow a portion of the radiation to pass within the desired blocking contour from the first side to the second side, wherein the portion of the radiation conforms to the desired blocking contour; and
recombination means for recombining the portion of the radiation conforming to the desired blocking contour into the desired spectral intensity profile; and
an optical illumination pathway having an input end and an output end, the input end configured to receive the radiation having the desired spectral intensity profile from the recombination means, and the output end being configured to provide the radiation having the desired spectral intensity profile to a biological sample.

* * * * *